United States Patent
Panattoni et al.

(10) Patent No.: US 6,986,836 B2
(45) Date of Patent: Jan. 17, 2006

(54) ELECTROPHORESIS GELS WITH INCORPORATED INDICIA

(75) Inventors: Cory M. Panattoni, Winters, CA (US); Donald E. Gueffroy, Davis, CA (US); Roger S. Provost, Napa, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 234 days.

(21) Appl. No.: 10/408,835

(22) Filed: Apr. 3, 2003

(65) Prior Publication Data

US 2004/0195102 A1 Oct. 7, 2004

(51) Int. Cl.
*G01N 27/26* (2006.01)
*G01N 27/403* (2006.01)
*G01N 27/453* (2006.01)

(52) U.S. Cl. ............... 204/466; 204/456; 204/470; 204/606; 204/616

(58) Field of Classification Search ......... 204/456–470, 204/606–621; 264/132, 259, 509
See application file for complete search history.

(56) References Cited

U.S. PATENT DOCUMENTS 4,415,428 A * 11/1983 Nochumson et al. ....... 204/606
5,569,369 A * 10/1996 Leffler et al. ............... 204/620
6,521,111 B1 * 2/2003 Amshey et al. ............. 204/616

* cited by examiner

*Primary Examiner*—Nam Nguyen
*Assistant Examiner*—Jeffrey T. Barton
(74) *Attorney, Agent, or Firm*—Townsend and Townsend and Crew LLP

(57) ABSTRACT

An electrophoresis gel is prepared with indicia incorporated into the gel itself rather than on a label or backing that is adhered to the gel. According to one method, the indicia are applied by first coating a solid surface that will be used as one internal surface of a gel mold with a solution of a water-permeable polymer, allowing the coating to dry, imprinting indicia in ink on the dry coating, and then forming the gel over the coating. In a variation on this method, the indicia are applied to a sheet which is then placed against the mold surface, the sheet being either a liner that is separable from the gel yet coated with the polymer or a sheet of the polymer itself. Alternatively, the indicia are printed directly on the mold surface without first coating the surface. This is achieved by using as a printing composition a mixture of an ink and a solution of a water-permeable polymer, then forming the gel over the imprinted indicia.

47 Claims, No Drawings

ELECTROPHORESIS GELS WITH INCORPORATED INDICIA

BACKGROUND OF THE INVENTION

1. Field of the Invention

This invention resides in the field of gel electrophoresis, and addresses in particular the concerns and difficulties associated with attaching labels, markings and other indicia to slab gels for various purposes.

2. Description of the Prior Art

Gel electrophoresis is one of the most widely used analytical procedures in biotechnology for the separation of both proteins and nucleic acids from complex samples. Gel electrophoresis offers a sensitive, rapid means of separating, identifying and quantifying biologically relevant molecules. The configuration and size of the gel can vary, depending on the type of separation. Slab gels, for example, are particularly useful since they permit separations to be performed in either one or two dimensions, and the resulting bands or spots can be observed directly or visualized, recorded and analyzed by instrumentation. In one-dimensional slab gel separations, a large number of samples can be separated side-by-side in a single gel and analyzed simultaneously. In two-dimensional slab gel separations, thousands of proteins from a single sample can be resolved in a single gel typically by first using isoelectric focusing to separate the proteins into bands in one dimension and then using sodium dodecylsulfate polyacrylamide gel electrophoresis to further separate the proteins in each band in the second dimension. Tube gels or strip gels are typically used for the first dimension separation. Once separated, the molecules of interest can be detected and identified or quantified directly by comparison to standards, or interrogated further by diverse methods such as hybridization to tagged probes, immunochemical detection or analysis by mass spectrometry.

The reading of a gel can be performed either visually by the user or by automated detection systems. Certain indicia are often included in the reading procedure to assist in the identification of the sample components and to minimize the occurrence of errors. These indicia may consist of gel orientation guides, migration distance indicators, lane indicators, sample identifiers, the supplier's catalog numbers, and even the supplier's logo. Barcodes may be used to provide some of these indicia, while others may be simple letters, numbers or grid lines and similar markings. Indicia can also help avoid mistaking one gel for another when different gels have been simultaneously stained and washed, as is typically done prior to the reading of a gel to make the bands or spots readily detectable. Many of these concerns are present in tube gels as well, particularly those that serve as the first dimension in a two-dimensional separation. Tube gels would benefit not only from identifying indicia, but also from alignment markings that would alert the technician when a portion of the gel has been stretched or otherwise distorted.

Indicia can thus be useful in many ways, but to be effective, the indicia must not interfere with the electrophoretic separation or impose limitations on the processing and handling of the gel that occur after the separation is completed. These needs have presented a challenge to gel manufacturers and users.

A common means of applying indicia in the prior art is the embedding of a paper label in the gel. As the gel becomes enlarged during processing, however, paper labels often curl and tear, and even when they remain intact, paper labels tend to become stained, obscuring the indicia. A gel labeling method that does not involve the use of paper labels is disclosed in United States Patent Application Publication No. US 2003/0038030 A1, publication date Feb. 27, 2003, filing date Sep. 20, 2002. The method in this publication involves the use of a backing consisting of a solid transparent sheet on one side of the gel. The gel is chemically bonded to the backing to assure secure adherence, and the desired indicia are imprinted on the backing sheet. The gel is formed over the backing by polymerizing the gel from a monomer solution that is in direct contact with the backing while forming covalent bonds between the gel and functional groups on the backing. Other backing sheets are disclosed in U.S. Pat. No. 4,415,428, issued Nov. 15, 1988, on an application filed Jan. 27, 1982.

Backing sheets have also been used that adhere to the gel by means other than covalent bonds. Unfortunately, backing sheets that are not bonded to the gel are susceptible to detachment from the gel, particularly during the handling or processing of the gel after electrophoresis, which results in loss of the indicia. Regardless of how the backing sheet is made to adhere to the gel, the sheet itself presents problems during the staining of the gel. Staining is typically performed by immersing the gel in a staining solution and allowing the solution to penetrate the gel from all sides. When this is done with gels that have a backing sheet, penetration occurs only from the exposed side, and this requires more time for proper staining to occur. This results in low efficiency, sensitivity and reliability.

It would seem that some of these problems could be eliminated by using only a partial backing sheet or a label of smaller dimensions than the gel, leaving the remainder of the gel exposed on both sides. This would not be suitable for all types of indicia, but for those for which a small label would suffice, further problems would arise. When a gel to which a small label is attached is removed from a gel cassette for staining and analysis, for example, the chances that the gel will break are particularly high. One reason is that the gel in the area adhering to the label is less flexible and less able to stretch than areas of the gel that are not constricted by the label, and this difference makes the gel particularly vulnerable to breakage at locations close to the edges of the label. This vulnerability is made even greater when the gel is immersed in solutions for applying stains and for removing excess stain, since these solutions can cause a gel to enlarge or shrink by as much as 30%. Gels with small labels are also susceptible to the formation of extensive cracks emanating from the label when the gels are dried for long-term storage.

SUMMARY OF THE INVENTION

These and other concerns are addressed by the present invention, which resides in a method for forming an electrophoresis gel with indicia that are incorporated directly in the gel, that do not interfere with solute migration or become distorted during electrophoresis, and that do not impose dimensional restriction to the gel, i.e., do not prevent the gel from expanding, contracting, or stretching during the staining, washing, drying, or handling that typically occur in the processing steps that follow an electrophoretic separation. The invention also resides in gels bearing indicia incorporated by this method and in various components used in forming gels bearing these indicia.

The indicia are incorporated in the gel by any of several methods in accordance with this invention. According to one method, a coating or film of water-permeable polymer is applied over the internal surface of a gel mold, the coating or film if applied wet is allowed to dry, and the indicia are applied to the coating or film with a suitable ink. A gel is then cast in the mold over the imprinted coating or film without becoming bonded to the surface of the mold. The surface to which the indicia are applied in this manner can be any inside surface of the mold cavity wetted by the gel-forming reagents. For slab gels, the surface can be one of the two flat plates of a cassette or the flat bottom plate of an open casting tray for a slab gel, while for tube gels, strip gels, or gels of other configurations that are cast in two-part molds, the coated surface can be the internal surface of any single part of the mold. Since neither the gel nor the water-permeable polymer are bonded to the surface of the mold, the gel, which incorporates the water-permeable polymer, can be removed from the mold with the indicia remaining intact in the gel.

In a second method, the indicia are applied to a flexible solid sheet that has been coated on one side with a water-permeable polymer. The solid sheet itself is not water-permeable, and the indicia are placed on the coated side of the sheet. The flexible sheet is placed over the surface of a glass or plastic plate or mold part, either before or after the indicia have been applied, with the polymer coating and indicia facing away from the glass or plastic. The sheet can be simply placed against the glass or plastic or is adhered to the glass or plastic by an adhesive. Either way, the gel is cast in the mold with the sheet as a liner, and electrophoresis is performed in the cast gel. Following electrophoresis, the gel, which incorporates both the polymer from the coating and the indicia and is not bonded to the flexible sheet, is removed from the mold and readily separated from the flexible sheet or liner. The liner will generally remain adhered to the mold surface although the adherence can be strengthened by the use of an adhesive between the liner and the surface.

In a third method, the indicia are applied to a dry film of the water-permeable polymer which has been previously prepared outside the mold, and the indicia are applied before the film is placed in contact with the mold surface. The indicia-bearing film is then placed over the mold surface and the gel is cast in the mold. Here again, the resulting gel incorporates the water-permeable polymer and the indicia, and is readily removable from the mold after electrophoresis is performed since neither the gel, the polymer, nor the indicia are bonded to the mold surface.

In a fourth method, the indicia are imprinted directly on the internal surface of the mold by applying a printing medium consisting of a solution or suspension of the ink or pigment in a liquid solution of a water-soluble polymer. The indicia are then allowed to dry by evaporation of the solvent or suspending agent, and the gel is then cast over the dried indicia. Electrophoresis is then performed, and the gel is removed from the mold with the polymer and indicia as part of the gel.

In the typical electrophoretic procedure, the mold in which the gel is cast also serves as the enclosure in which the gel is retained during electrophoresis. In slab gels, for example, the plates of a gel cassette serve as both the mold and the retaining walls during electrophoresis. In two-dimensional electrophoresis, the tube or strip gel used in the first-dimension separation is an exception, since the second dimension separation is performed by first removing the tube or strip gel from its enclosure and then placing it along the edge of a slab gel before performing the second dimension separation.

This invention further resides in electrophoresis gels prepared by any of the methods described above and in kits for use in applying indicia to gels by these methods. One type of kit includes a flexible solid sheet of water-impermeable material coated on one side with a dry water-permeable polymer ready for the application of indicia, plus an appropriate ink that the water-permeable polymer will retain, or a writing or printing implement that can transfer the ink to the polymer surface according to the desired indicia. Another type of kit includes a sheet of the water-permeable polymer itself in dry form ready for the application of indicia, plus the same type of ink or writing or printing implement.

In embodiments of this invention that involve the application of indicia over a sheet of polymer or a polymer coating, suitable inks are those that adhere to the sheet or coating, whereas in embodiments of this invention where the ink is combined with a solution or suspension of the polymer to form an ink composition, suitable inks are those that are readily dissolved or suspended in the composition and compatible with the polymer. In all of these variations, preferred inks are those that neither dissolve in the gel-forming reagents during the casting of the gel nor inhibit polymerization of the gel, and that remain stable in the gel for the shelf life of the gel.

These and other features, objects, and advantages of the invention and its preferred embodiments are described in more detail below.

DETAILED DESCRIPTION OF THE INVENTION AND PREFERRED EMBODIMENTS

Gels to which this invention are most readily applicable are those that are cast in a mold that can be opened to expose its internal surfaces. Examples are slab gels that are cast in cassettes constructed of two flat plates separated by spacers, cylindrical gels that are cast in the annular space between two concentric cylinders, and strip gels that are cast in two-part molds. Descriptions of slab gel cassettes are found in U.S. Pat. No. 4,572,040, entitled "Apparatus for Vertical Gel Electrophoresis," issued Mar. 4, 1986, on an application filed Sep. 26, 1984, and U.S. Pat. No. 6,162,342, entitled "Rapid Assembly Casting System for Slab Gels," issued Dec. 19, 2000, on an application filed Feb. 12, 1999. A description of cylindrical gels cast in the annular space between two cylinders is found in U.S. Pat. No. 5,938,909, entitled "Cup-Shaped Vertical Slab Gel Electrophoresis Apparatus," issued August 117, 1999, on an application filed Mar. 14, 1997. A description of strip gels cast in two-part molds is found in co-pending U.S. patent application Ser. No. 10/095,563, filed Mar. 11, 2002, entitled "Assembly for casting and use of an isoelectric focusing strip." The molds described in application Ser. No. 10/095,563 are rod-shaped molds split longitudinally into two halves, each half having a half-circle profile and a flat contacting surface with a groove of rectangular cross section in each contacting surface. The contents of each of the patents cited in this paragraph and elsewhere throughout this specification are incorporated herein by reference in their entirety. For slab gels or cup-shaped gels, the indicia are applied to the internal surface of one of the two flat plates, and for strip gels formed in two-part molds, the indicia are applied in one of the grooves.

In embodiments of the invention in which the indicia are applied to an intermediary liner sheet that does not become part of the gel, the liner sheet can be made of any inert, flexible, and preferably transparent material that can be coated with a water-permeable polymer on one side and will not bond to the gel as the gel is formed. While the coating material is a water-permeable polymer, the sheet itself is preferably not water-permeable. Examples of materials from which the sheet can be made are MYLAR® and other polyesters, polymethylpentene, polystyrene, polypropylene, polyethylene, styrene-acrylonitrile copolymers (SAN), polycarbonate, cellulose acetate propionate, cellulose acetate butyrate, nitrile-acrylonitrile-styrene copolymers, acrylics (thermoplastic polymers and copolymers of acrylic acids), poly(ethylene terephthalate) (PET), polymethacrylate, methyl methacrylate copolymers (NAS), and acrylonitrile-butadiene-styrene copolymers. The thickness of the sheet is not critical and can vary provided that the sheet remains flexible. Best results will generally be achieved with thicknesses ranging from about 0.05 mm to about 0.5 mm. If desired, adhesion of the sheet to the mold surface when the gel is removed can be improved by coating the sheet with an adhesive on the side opposite the side bearing the water-permeable polymer. Any conventional adhesive can be used, preferably a pressure-sensitive adhesive which generally includes an elastomeric polymer and a tackifying agent. Typical elastomeric polymers are butyl rubbers, poly(vinyl ether)s, acrylics, and silicones.

In embodiments of the invention in which the indicia are applied to a dry sheet of water-permeable polymer before the sheet is applied to the mold surface, the dry sheet can be formed by the simple casting of a sheet from a solution or suspension of the polymer and allowing the solvent or suspending agent to evaporate. Once the indicia are applied and the sheet is placed over the mold surface, the polymer then functions in the same manner as the polymer in the coatings that are applied to the mold surface before indicia are applied, i.e., the sheet becomes is incorporated into the gel.

In embodiments of the invention in which the mold surface, or a liner that adheres to the mold surface when the gel is removed, is coated with a polymer before the indicia are applied, as well as embodiments in which the indicia are applied to a sheet of the polymer itself rather than to a liner with a polymer coating, the polymer may be the same as or different than the polymer used to form the bulk of the gel. As noted above, the polymer is one which when dry is permeable by water and whose chains are compatible with the polymer chains of the gel once the gel is formed. Examples of polymers that can be used for these embodiments are linear polyacrylamide, linear polyacrylamide derivatives, poly(vinyl alcohol), poly(vinyl pyrrolidone), poly(ethylene glycol), poly(ethylene oxide), dextran, water-soluble celluloses, starch, and agarose. In this specification and the appended claims, "linear polyacrylamide derivatives" include polyacrylamides bearing substituent groups that improve the water permeability and/or water solubility of the polyacrylamide. Examples are poly(methacrylamide), poly(N-acryloylaminopropanol), and poly(N-acryloylamino-ethoxyethanol). The term "water-soluble celluloses" likewise includes modified celluloses such as those known in the art and have properties similar to cellulose. Examples are methylcellulose, ethylcellulose, hydroxymethylcellulose, and hydroxyethylcellulose.

The term "water-permeable polymer" refers to a polymer which when dry and placed in contact with water or an aqueous solution will allow the water or the solution to penetrate the polymer network. The term includes polymers that are soluble in water, i.e., those that dissolve readily in water as well as those that dissolve slowly or only with agitation. The term also includes polymers that swell and/or become gelatinous upon absorption of water.

The water-permeable polymer can be either a crosslinked polymer or a linear polymer (not crosslinked). When the gel is formed over the polymer, the polymer is incorporated into the gel rather than forming a solid skin over the gel surface. The bulk gel and the polymer together form a continuous gel with no physical discontinuity or interface at the gel depth where the surface of the polymer when dry was originally located. For gels whose bulk composition is a crosslinked polymer, a particularly preferred water-permeable polymer is one that is formed of a linear version of the same polymer used in crosslinked form in the bulk of the gel. When a linear polymer is used and is applied as a coating on the mold surface, the coating can be formed from a solution of the polymer or from a solution of a monomer and any additive (s) necessary to effect polymerization of the monomer once it has been applied to the surface. When a monomer solution is used, the monomer solution can contain a catalyst, an initiator, or both, if necessary to achieve polymerization, without a crosslinking agent, and polymerization of the monomer into a linear polymer can occur in the coating itself. Preferably, however, the coating is formed by applying a liquid solution of a pre-polymerized linear polymer, and the coating is dried by simply allowing the solvent to evaporate.

When the gel to be formed is a polyacrylamide gel, for example, a coating of linear polyacrylamide can be formed by applying linear polyacrylamide in solution, aqueous or otherwise, to the solid surface and allowing the solvent to evaporate. Preferred linear polyacrylamides are those having a weight-average molecular weight of from about 1,000 to about 10,000,000. The concentration of the linear polyacrylamide can vary and is not critical to the invention. The optimal concentration may depend on the molecular weight of the polymer. A low molecular weight linear polyacrylamide, such as one whose molecular weight is 1,500, may be used at a high concentration such as 50% by weight, while a high molecular weight linear polyacrylamide, one with a molecular weight of 5,000,000 to 6,000,000 for example, may be used at a low concentration such as 2% by weight. In some cases, a mixture of both high and low molecular weight linear polyacrylamides will be beneficial. Once the linear polyacrylamide coating is formed, regardless of its molecular weight, the bulk gel can then be cast over the coating from a solution of acrylamide monomer and a crosslinking agent, in the concentration ranges listed above, together with other additives as needed. Polymerization of the monomer and crosslinking agent will result in a polymeric network that is integral with and inseparable from the film. Although not to be bound by any particular theory, one explanation for the integral character of the resulting gel is that during the polymerization reaction, the monomer penetrates the network of linear polyacrylamide chains in the film and polymerizes around the chains to form an intertwined network of chains, including those that are crosslinked and those that are not crosslinked.

For gels that are formed by means other than polymerization, such as agarose which gels upon cooling from a warm aqueous solution, the film or sheet and the bulk of the gel can be formed from solutions of the same materials. When the film is first applied as a coating over the mold surface, the coating is allowed to dry before the indicia are applied, and the entire gel is cooled after the gel solution forming the bulk of the gel has been added.

The application of a coating in the practice of this invention can be achieved by conventional methods, such as by the use of a brush or a pad or by spraying or dipping.

In embodiments in which the indicia are applied as a solution or suspension of the ink in a liquid polymer solution, and application is made directly to the mold surface or to a liner that has been adhered to the surface, the polymer is preferably a water-soluble polymer. As noted above, certain polymers will meet both the definition of a water-permeable polymer and the definition of a water-soluble polymer. When there is a difference, it may be simply a matter of the rate of dissolving or the consistency or viscosity of the resulting solution. When the ink is suspended or dissolved in the liquid polymer solution, the composition will be sufficiently fluid (i.e., of sufficiently low viscosity) that it can function as an ink and is thereby capable of being applied with a writing or printing implement. The polymer in these embodiments may be the same as or different than the polymer used to form the bulk of the gel. The considerations discussed above regarding compatibility of the polymer with the gel apply here as well, i.e., the polymer in the ink formulation should be compatible with the polymer forming the bulk of the gel. Here again, preferred polymers for the ink formulation are linear polymers that dry readily by evaporation of the solvent or suspending agent.

The term "gel-forming liquid" is used herein to denote conventional liquid preparations that are poured, pumped, or otherwise placed inside gel molds where they are allowed to solidify into gels suitable for electrophoresis. As noted above, the mold for a slab gel typically consists of two flat plates separated by spacers that define the thickness or depth of the gel. Molds for gels of other configurations, such as tube gels, gel strips, and continuous closed cylindrical gels, are shaped accordingly. The gel-forming liquid may be a monomer solution that is allowed to polymerize in the mold cavity. Alternatively, the gel-forming liquid may be a solution of a polymer or other material that is placed in the cavity and then exposed to heat or any other form of energy that will cause the material to solidify into a gel. A further alternative is a gel solution that is hot when added to the cavity and then gels upon cooling.

The most notable examples of gel materials are polyacrylamide, polyacrylamide derivatives, agarose and starch. The liquid from which the gel is typically formed is a solution of monomer or other gel-forming material, and the gel is prepared by filling the gel mold, enclosure, or cassette with the solution and allowing the solution to solidify into a gel. The components used in forming the gels and the procedures are well known among those skilled in gel electrophoresis. Preferred gels are those made of crosslinked polyacrylamide, and are typically formed from an aqueous solution containing acrylamide monomer, a crosslinking agent, a catalyst and an initiator. The amounts of each of these components can vary widely, and the choice will depend on the concentrations and molecular weights of the solutes to be separated, as well as the type of electrophoretic separation, i.e., isoelectric focusing, a two-dimensional separation, a gradient gel separation, a pulsed or oscillating field separation, isotachophoresis, or any of the various electrophoretic procedures that are known in the art. For polyacrylamide gels, the monomer concentration in the starting solution may range from about 3% to about 30% by weight of the solution itself, while the crosslinker may constitute from about 0.5% to about 10% of the monomer/crosslinker combination.

Inks that can be used in the practice of this invention include any conventional ink or pigment formulation that when dried is insoluble in the gel-forming liquid used to form the bulk of the gel and therefore does not "run," "bleed," or otherwise produce indicia that become distorted when placed in contact with the bulk gel liquid. Since gel-forming liquids are typically aqueous solutions, preferred inks are those that when dried are insoluble in water and therefore will not diffuse into the bulk of the gel. Inks that contain a solid pigment dispersed in water or in an organic liquid that is miscible with water, such as aqueous or alcohol-based solutions or suspensions, can be used provided that the ink is a permanent ink that once dried will not diffuse into the gel solution. Other inks suitable for use are fluorescent inks, inks that are visible only in ultraviolet light, and inks that are visible in both visible light and ultraviolet light.

In embodiments in which the ink is applied as a mixture with a solution of polymer directly to the mold surface without first coating the solid surface with a water-permeable polymer, the relative amounts of ink and polymer solution may vary and are not critical to the success of the invention. For certain inks, higher proportions of ink will generally produce darker indicia, and the proportion of ink to polymer may affect the viscosity of the mixture and hence the ease with which it can be applied. Viscosity limitations may be imposed by the implement used to apply to the mixture to the plate, i.e., whether a pen or a stamp is used, the fineness of the lines, and similar considerations. Certain inks, such as those that are readable by instrumentation, require only very small amounts, while those that are read visually will benefit from higher amounts. Fluorescent inks, for example, can be used effectively in concentrations substantially less than 1% by weight. User-visible inks, on the other hand, are preferably used in concentrations exceeding 5% by weight. Some will read best at concentrations ranging from about 20% to about 80% ink by weight, preferably from about 35% to about 65%. In one embodiment successfully tested by the inventors herein, a 50% mixture was used. The optimum amount for each ink is readily determinable by routine experimentation using simple trial and error.

When the ink is applied over a coating of the dried gel-forming material, application (i.e., the formation of the indicia) can be made by hand using an implement such as a felt-tip pen, a capillary pen, a stylus, or a brush. Mechanical printing techniques, such as offset printing, lithography, or inkjet printing, can also be used. Inkjet printing can be performed using convention inkjet printers and inks, such as a VIDEOJET EXCEL 273SE Inkjet Printer (Videojet Technologies, Inc., Wood Dale, Ill., USA) with HR W/16-5600 ink. The same techniques can be used when the ink is applied directly to the plate as a mixture with the gel-forming liquid.

The term "indicia" is used herein to denote markings of any kind. If the gel is a precast gel, the indicia may be the type of information that might be incorporated by the manufacturer, including, but not limited to, a barcode, a set of grid lines across the entire gel, length indicators (i.e., "rulers") along the edge of the gel, lane numbers, reference points for manual or automated detection, a supplier catalog number, a supplier logo, or information regarding the gel composition such as its gel type or gel percentage. Alternatively, the indicia may be markings that can be applied by the user for gels that are prepared at the user site, such as a sample code number or other identifiers, the name of the user, the date on which the gel was prepared or the separation was performed, and the composition of the gel, including information relating to concentrations or gradients.

In those embodiments of the invention in which a polymer coating is first applied to the mold surface, or to one plate or one internal face of the mold, the coating can be applied to the entire plate or internal face or to only the portion where indicia are needed. The choice will often depend on the type of indicia to be applied. When the indicia are grid lines, for example, the coating preferably covers the entire plate. When the indicia are a bar code, the coating is only needed in the region where the bar code will reside. Coating areas for other indicia will be readily apparent to those skilled in the manufacture or use of electrophoresis gels.

Once the indicia are applied, either to a coating, a coated liner, or a sheet of the coating material, or directly to the internal surface of the gel mold, the mold is closed and filled with the gel-forming liquid. For slab gels, indicia are applied to one of the two flat plates of the mold and the mold is closed by combining the imprinted plate with the remaining plate and appropriate spacers as needed to form a conventional slab gel enclosure or cassette. For gels of other configurations, the molds are formed appropriately, as will be evident to those skilled in the use of these molds and the formation of electrophoresis gels in general. Cassettes, plates and gel enclosures of various kinds are well known in the art and widely available from commercial suppliers.

The solid surfaces to which the indicia are applied, either directly, through a coating, or through a coating on a liner, can be formed of any material that is known for use as a structural material for a gel mold. Examples are glass and various plastics such as acrylics (thermoplastic polymers and copolymers of acrylic acids), polystyrene, polycarbonate, poly(ethylene naphthalate) (PEN), poly(ethylene terephthalate) (PET), poly(ethylene terephthalate glycolate) (PETG), styrene-acrylonitrile copolymer (SAN), and methyl methacrylate-styrene copolymers (NAS).

The following examples are offered only as illustration.

EXAMPLE 1

This example illustrates the application of indicia by hand to a glass plate whose entire surface on one side is coated with linear polyacrylamide, the indicia being formed in ink from common ink pens and also in india ink.

A flat glass plate was coated with a 2% aqueous solution of linear polyacrylamide having a weight-average molecular weight of 5,000,000 to 6,000,000, and the coating was allowed to dry. (All percents in these examples are by weight unless otherwise noted.) Markings were then applied by hand to the dry coating in separate lines with different common writing pens—three Sanford Sharpies (Series 35000 porous tip permanent markers, one black, one blue and one red; supplier: PenCity, Ellijay, Ga., USA), one standard ballpoint pen, and one Stanford Rolling Writer. India ink was applied by a wooden rod dipped in the ink. Each ink was allowed to dry before proceeding further.

Thus marked, the plate was combined with other cassette components to form a gel cassette with a gap width of 1.0 mm. A polyacrylamide gel was then cast in the cassette from an aqueous acrylamide monomer solution consisting of 12% T, 2.6% C (i.e., monomer and crosslinker combined at a total concentration of 12%, with the crosslinker constituting 2.5% of the monomer/crosslinker combination), and catalyst and initiator in appropriate quantities. As polymerization proceeded, the coating and the markings became one with the gel and remained a part of the gel after the gel was removed from the cassette. By visual observation, the indicia written by the three Sanford Sharpie pens and the ball point pen were all clear, sharp and easily readable. The indicia applied by the Rolling Writer inhibited polymerization, and the indicia applied by the india ink had smeared.

EXAMPLE 2

This example is a further illustration of the application of indicia by a common ink pen to a glass plate coated with linear polyacrylamide, using two different concentrations of linear polyacrylamide in separate tests.

A flat glass plate was coated with a 2% aqueous solution of linear polyacrylamide having a weight-average molecular weight of 5,000,000 to 6,000,000. A separate glass plate was coated with a 50% aqueous solution of linear polyacrylamide with a weight-average molecular weight of 1,500. Both plates were allowed to dry. Markings were then applied by hand to the coated sides of each plate using a black permanent marker (Stanford Sharpie).

Each plate was then combined with other cassette components to form a gel cassette with a gap width of 1.0 mm. A polyacrylamide gel was then cast in the cassette from a monomer solution identical to that of Example 1. As polymerization proceeded, each coating and the markings applied to the coatings became part of the respective gel and remained so after the gel was removed from the cassette. Visual observations indicated that the markings on both gels were clear and sharp and easily readable.

EXAMPLE 3

This example illustrates the application of indicia by an inkjet printer to a glass plate coated with linear polyacrylamide.

A flat glass plate identical to that of Example 1 was coated with a 2% aqueous solution of linear polyacrylamide having a weight-average molecular weight of 5,000,000 to 6,000,000. The coating was allowed to dry and was then imprinted with a barcode using a VIDEOJET EXCEL 273 SE Ink Jet printer with HT W/16-5600 ink. A polyacrylamide gel was then cast in a cassette of which the plate formed one side, using a monomer solution identical to that of the preceding examples. The resulting gel was then removed from the cassette. The barcode remained intact on the gel upon removal of the gel from the cassette. Even after the gel was dried according to typical procedure following electrophoresis, the barcode remained intact and readable.

EXAMPLE 4

This example illustrates the application of indicia to a glass plate by marking the bare plate with india ink mixed with an aqueous solution of linear polyacrylamide.

A glass plate that was not precoated with linear polyacrylamide was used. Two ink/polyacrylamide mixtures were prepared, both formed by combining equal volumes of india ink and aqueous linear polyacrylamide. The linear polyacrylamide used in the first mixture was a 0.75% aqueous solution and that used in the second was a 2% aqueous solution, both by weight and both prior to addition of the india ink. The ink/polyacrylamide mixtures were applied as markings to separate areas of the plate by a wooden stick dipped in each mixture. The markings were then allowed to dry and a cassette was assembled from the plate. A gel was formed in the cassette, using a monomer solution identical to those of the preceding examples. The gel was then removed form the cassette.

The markings from both mixtures were present on the gel even after removal from the cassette. Smearing of the markings occurred but the markings were still readable. The smearing occurred during the polymerization and did not continue after polymerization was complete. The least amount of smearing occurred with the higher concentration of linear polyacrylamide.

EXAMPLE 5

This example illustrates the application of indicia to a flexible liner sheet coated with linear polyacrylamide.

A sheet of polypropylene was coated on one side with the same 2% linear polyacrylamide solution used in Example 1 above, and the coating was allowed to dry. The coated sheet, which did not have an adhesive on its uncoated side, was then placed against a flat glass plate, and markings were placed on the sheet by hand using a black Stanford sharpie as described in Example 1. The plate was then combined with another plate and spacers to form a slab gel cassette, and a 12% polyacrylamide gel was cast in the cassette. Upon subsequent removal of the gel from the cassette, the polypropylene sheet remained adhered to the glass plate while the linear polyacrylamide coating and the markings were incorporated in the gel.

The foregoing description is offered primarily for purposes of illustration. Further modifications, substitutions and variations will be apparent to those skilled in the art and will be included within the scope of the invention.

What is claimed is:

1. A method for forming an electrophoresis gel marked with detectable indicia, said method comprising the steps of:
    (a) forming said indicia in ink on a dry film of a water-permeable polymer that is capable of receiving said ink;
    (b) placing an aqueous gel-forming liquid in a gel mold having an internal surface with said indicia-bearing film layered over said surface but not bonded thereto, and allowing said gel-forming liquid to permeate said film; and
    (c) converting said gel-forming liquid, thus placed in said mold, into a gel that incorporates both said water-permeable polymer and said indicia and is not bonded to said internal surface, with neither said water-permeable polymer nor said indicia imposing dimensional restriction to said gel.

2. A method in accordance with claim 1 in which step (a) comprises applying said indicia to a solid surface previously coated with said dry film, and step (b) comprises utilizing said solid surface as said internal surface of said gel mold.

3. A method in accordance with claim 1 in which step (a) comprises applying said indicia to said dry film while said dry film is not in contact with said gel mold, and said method further comprises placing said dry film against said internal surface of said gel mold between steps (a) and (b).

4. A method in accordance with claim 1 in which said internal surface is a first flat plate and said gel mold is a slab gel mold defined by said first flat plate and a second flat plate separated from said first flat plate by spacers.

5. A method in accordance with claim 1 in which said internal surface is a curved surface, and said gel mold is a member selected from the group consisting of a tubular gel mold and a closed cylindrical sheet gel mold.

6. A method in accordance with claim 1 in which said dry film is a coating on one side of a flexible solid sheet but is not bonded to said flexible solid sheet, and in step (b) said flexible solid sheet is interleaved between said dry film and said internal surface.

7. A method in accordance with claim 1 in which said water-permeable polymer is a member selected from the group consisting of linear polyacrylamide, linear polyacrylamide derivatives, poly(vinyl alcohol), poly(vinyl pyrrolidone), poly(ethylene glycol), poly(ethylene oxide), dextran, water-soluble celluloses, starch, and agarose.

8. A method in accordance with claim 1 in which said water-permeable polymer is a member selected from the group consisting of linear polyacrylamide, poly(vinyl alcohol), poly(vinyl pyrrolidone), poly(ethylene glycol), poly(ethylene oxide), dextran, water-soluble celluloses, starch, and agarose.

9. A method in accordance with claim 1 in which said water-permeable polymer is linear polyacrylamide.

10. A method in accordance with claim 1 in which said water-permeable polymer is linear polyacrylamide and said gel-forming liquid is an aqueous solution comprising acrylamide and a crosslinking agent.

11. A method for forming an electrophoresis gel marked with detectable indicia, said method comprising the steps of:
    (i) forming indicia on a solid surface by applying to said surface, in a pattern corresponding to said indicia, a composition comprising an ink dispersed in a solution of a water-soluble polymer in a solvent, and evaporating said solvent to leave said indicia formed by said ink and said polymer on said surface,
    (ii) placing an aqueous gel-forming liquid in a gel mold having an internal surface consisting of said solid surface with said indicia thereon, and
    (iii) converting said gel-forming liquid, thus placed in said mold, into a gel that incorporates said indicia.

12. A method in accordance with claim 11 in which said water-soluble polymer is a member selected from the group consisting of linear polyacrylamide, linear polyacrylamide derivatives, poly(vinyl alcohol), poly(vinyl pyrrolidone), poly(ethylene glycol), poly(ethylene oxide), dextrans, water-soluble celluloses, starch, and agarose.

13. A method in accordance with claim 11 in which said water-soluble polymer is a member selected from the group consisting of linear polyacrylamide, poly(vinyl alcohol), poly(vinyl pyrrolidone), poly(ethylene glycol), poly(ethylene oxide), dextran, water-soluble celluloses, starch, and agarose.

14. A method in accordance with claim 11 in which said water-soluble polymer is linear polyacrylamide.

15. A method in accordance with claim 11 in which said water-soluble polymer is linear polyacrylamide and said gel-forming liquid is an aqueous solution comprising acrylamide and a crosslinking agent.

16. A method in accordance with claim 1 or 11 in which said gel-forming liquid is a solution of a member selected from the group consisting of polyacrylamide, polyacrylamide derivatives, agarose and starch.

17. A method in accordance with claim 1 or 11 in which said indicia are a member selected from the group consisting of (1) indicia identifying a manufacturer of said slab gel, (2) a catalog number, and (3) indicia identifying a gel type.

18. A method in accordance with claim 1 or 11 in which said indicia are a bar code.

19. A method in accordance with claim 1 or 11 in which said indicia are a member selected from the group consisting of (1) a grid pattern and (2) markings indicating solute migration distances along said gel.

20. A method in accordance with claim 1 or 11 in which said indicia are reference spots for comparing solutes of a sample to known solutes.

21. A method in accordance with claim 1 or 11 in which step (a) comprises machine printing of said indicia.

22. A method in accordance with claim 1 or 11 in which step (a) comprises manually applying said indicia.

23. A method in accordance with claim 1 or 11 in which said ink is a visible pigment.

24. A method in accordance with claim 1 or 11 in which said ink is a fluorescent dye.

25. A method in accordance with claim 1 or 11 in which said ink is an ultraviolet dye.

26. A method in accordance with claim 1 or 11 in which said ink is a luminescent dye.

27. An electrophoresis gel having indicia incorporated in said gel and immobilized therein in a manner that does not permit migration of said indicia within said gel when an electric field is imposed across said gel and does not restrict the ability of said gel to expand or contract, wherein the indicia had been formed using an ink or pigment prior to formation of the electrophoresis gel.

28. An electrophoresis gel in accordance with claim 27 in which said gel is a slab gel.

29. An electrophoresis gel in accordance with claim 27 in which said gel is a polyacrylamide gel.

30. An electrophoresis gel in accordance with claim 27 in which said gel is an agarose gel.

31. An electrophoresis gel in accordance with claim 27 in which said gel is a starch gel.

32. An electrophoresis gel in accordance with claim 27 in which said indicia are formed in a visible pigment.

33. An electrophoresis gel in accordance with claim 27 in which said indicia are formed in a fluorescent dye.

34. An electrophoresis gel in accordance with claim 27 in which said indicia are formed in an ultraviolet dye.

35. An electrophoresis gel in accordance with claim 27 in which said indicia are formed in a luminescent dye.

36. An electrophoresis gel in accordance with claim 27 in which said indicia are a member selected from the group consisting of (1) indicia identifying a manufacturer of said slab gel, (2) a catalog number, and (3) indicia identifying a gel type.

37. An electrophoresis gel in accordance with claim 27 in which said indicia are a bar code.

38. An electrophoresis gel in accordance with claim 27 in which said indicia are a member selected from the group consisting of (1) a grid pattern and (2) markings indicating solute migration distances along said gel.

39. An electrophoresis gel in accordance with claim 27 in which said indicia are reference spots for comparing solutes of a sample to known solutes.

40. An electrophoresis gel having indicia incorporated therein by the method of claim 1.

41. A polyacrylamide electrophoresis gel having indicia incorporated therein by the method of claim 1.

42. An agarose electrophoresis gel having indicia incorporated therein by the method of claim 1.

43. A starch electrophoresis gel having indicia incorporated therein by the method of claim 1.

44. An electrophoresis gel having indicia incorporated therein by the method of claim 11.

45. A polyacrylamide electrophoresis gel having indicia incorporated therein by the method of claim 11.

46. An agarose electrophoresis gel having indicia incorporated therein by the method of claim 11.

47. A starch electrophoresis gel having indicia incorporated therein by the method of claim 11.

* * * * *